(12) United States Patent
Tenerz et al.

(10) Patent No.: US 7,285,097 B2
(45) Date of Patent: *Oct. 23, 2007

(54) TECHNIQUE TO CONFIRM CORRECT POSITIONING WITH RESPECT TO ARTERIAL WALL

(75) Inventors: Lars Tenerz, Uppsala (SE); Dan Åkerfeldt, Uppsala (SE)

(73) Assignee: Radi Medical System AB, Uppsala (SE)

( * ) Notice: Subject to any disclaimer, the term of this patent is extended or adjusted under 35 U.S.C. 154(b) by 73 days.

This patent is subject to a terminal disclaimer.

(21) Appl. No.: 10/798,784

(22) Filed: Mar. 12, 2004

(65) Prior Publication Data

US 2004/0243007 A1 Dec. 2, 2004

Related U.S. Application Data

(60) Continuation-in-part of application No. 10/704,556, filed on Nov. 12, 2003, which is a division of application No. 10/042,247, filed on Jan. 11, 2002, now Pat. No. 6,682,489.

(60) Provisional application No. 60/260,895, filed on Jan. 12, 2001.

(51) Int. Cl.
*A61B 5/02* (2006.01)

(52) U.S. Cl. .................. 600/486; 600/485; 600/481

(58) Field of Classification Search ............... 600/481, 600/488, 485, 486; 606/213–215, 139, 144, 606/148, 264

See application file for complete search history.

(56) References Cited

U.S. PATENT DOCUMENTS

| | | | |
|---|---|---|---|
| 5,290,231 A * | 3/1994 | Marcadis et al. | 604/96.01 |
| 5,395,330 A * | 3/1995 | Marcadis et al. | 604/102.02 |
| 5,431,639 A | 7/1995 | Shaw | |
| 5,456,694 A * | 10/1995 | Marin et al. | 623/1.11 |
| 5,569,296 A * | 10/1996 | Marin et al. | 606/198 |
| 5,613,974 A | 3/1997 | Andreas et al. | |
| 5,766,151 A * | 6/1998 | Valley et al. | 604/103.07 |
| 5,766,206 A * | 6/1998 | Wijkamp et al. | 606/213 |
| 5,795,325 A * | 8/1998 | Valley et al. | 604/509 |
| 5,814,016 A * | 9/1998 | Valley et al. | 604/96.01 |

(Continued)

FOREIGN PATENT DOCUMENTS

WO WO98/07372 A2 2/1998

(Continued)

OTHER PUBLICATIONS

U.S. Appl. No. 10/756,765, filed Jan. 14, 2004, Egnelov et al.

*Primary Examiner*—Charles A. Marmor, II
*Assistant Examiner*—Navin Natnithithadha
(74) *Attorney, Agent, or Firm*—Foley & Lardner LLP (57) ABSTRACT

Methods and systems related to sealing punctures in blood vessels (such as following an angio or PTCA procedure) are disclosed. The invention provides a system to sense the location of a distal portion of a member within a body. The system includes an introducer portion having a distal end adapted to be placed within a body and a pressure sensor. The pressure sensor is in fluid communication with the distal end and is adapted to provide a pulsation which can be sensed by an operator when the distal end is placed within a pulsating portion of the body.

17 Claims, 8 Drawing Sheets

U.S. PATENT DOCUMENTS

| | | | |
|---|---|---|---|
| 5,855,559 A | 1/1999 | Van Tassel et al. | |
| 6,007,563 A | 12/1999 | Nash et al. | |
| 6,090,130 A | 7/2000 | Nash et al. | |
| 6,159,178 A * | 12/2000 | Sharkawy et al. | 604/103.08 |
| 6,179,827 B1 * | 1/2001 | Davis et al. | 604/523 |
| 6,193,670 B1 | 2/2001 | Van Tassel et al. | |
| 6,302,898 B1 * | 10/2001 | Edwards et al. | 606/214 |
| 6,350,252 B2 * | 2/2002 | Ray et al. | 604/107 |
| 6,350,274 B1 * | 2/2002 | Li | 606/213 |
| 6,508,828 B1 | 1/2003 | Akerfeldt et al. | |
| 6,589,206 B1 * | 7/2003 | Sharkawy et al. | 604/96.01 |
| 6,592,547 B2 * | 7/2003 | Grimes et al. | 604/96.01 |
| 6,682,489 B2 * | 1/2004 | Tenerz et al. | 606/213 |
| 6,733,515 B1 * | 5/2004 | Edwards et al. | 606/214 |
| 2004/0098046 A1 | 5/2004 | Tenerz et al. | |
| 2004/0172059 A1 | 9/2004 | Tenerz et al. | |

FOREIGN PATENT DOCUMENTS

| | | |
|---|---|---|
| WO | WO98/19605 A1 | 5/1998 |
| WO | WO98/40016 A2 | 9/1998 |

* cited by examiner

TECHNIQUE TO CONFIRM CORRECT POSITIONING WITH RESPECT TO ARTERIAL WALL

CROSS-REFERENCE TO RELATED PATENT APPLICATIONS

This application is a continuation-in-part of application Ser. No. 10/704,556, filed Nov. 12, 2003; which is a divisional application of application Ser. No. 10/042,247, filed Jan. 11, 2002, now U.S. Pat. No. 6,682,489, which in turn claims the benefit of priority of U.S. Provisional Patent Application No. 60/260,895, filed Jan. 12, 2001. The entire contents of application Ser. No. 10/704,556; application Ser. No. 10/042,247 and the Provisional Application No. 60/260,895 are incorporated herein by reference.

Also, certain aspects of this invention are similar to aspects of the invention described in application Ser. No. 10/756,765, filed Jan. 14, 2004, whose entire contents are incorporated herein by reference.

BACKGROUND OF THE INVENTION

The invention relates to sealing punctures in tissues of living bodies. The invention can be used, for example, when sealing punctures in the walls of arteries (such as following an angio or PTCA procedure) or other blood vessels. Background and various details of such techniques can be found in application Ser. No. 09/704,726 entitled "Sealing Device and Wound Closure Device" and filed on Nov. 3, 2000 by Dan Åkerfeldt et al., now U.S. Pat. Nos. 6,508,828; 5,613,974 (Assigned to Perclose, Inc.); and U.S. Pat. No. 6,090,130 (assigned to Kensey Nash Corporation). The entire contents of this application and these two patents are incorporated herein by reference.

In the course of using sealing devices or anchors that are inserted into an artery, it is helpful to detect the position of the various components with respect to the arterial wall. If an introducer is positioned based on feeling, there is a risk that the introducer pops out from the artery, and it is almost impossible to reintroduce it in an easy way. Ideally, the seal or anchor is deployed as close to the puncture hole as possible. If the seal or anchor is deployed too deep in the artery, the risk increases that the seal or anchor will be caught upstream in the artery before being seated on the puncture hole and/or cause injury to the inside of the artery wall.

An introducer is normally 10-15 cm long, and during cauterization it is fully inserted. To seal the puncture hole, a seal needs to have a diameter larger than the introducer, e.g. >3 mm. To be properly seated to the inside of the artery hole, the seal needs to be even larger, otherwise the seal may be pulled out by mistake. The femoral artery inside diameter is normally 5-10 mm in humans, and it is difficult to increase the seal width to more than 5 mm because, if the seal width is bigger, it is difficult to fit the seal into the arterial lumen without affecting the circularity of the lumen too much. The length of the seal can however be increased to achieve high pull out strength.

The FEMOSEAL™ seal (described in U.S. Pat. No. 6,508,828) and Kensey Nash ANGIOSEAL™ seal anchors (described in 6,090,130) have a length of 10 mm, and consequently can the position and direction of the seal or anchor inserted in the artery are not guided. As discussed above, the seal or anchor can also be caught in an artery branch upstream. The ANGIOSEAL™ seal technique employs an anchor that can move around in the artery as its inner member. The anchor does not perform a sealing function (and is not a "seal" as this term is used in this patent specification) but instead anchors an outer member and the outer member performs the sealing function. The ANGIOSEAL™ seal technique solves the problem of detecting the position of the various components relative to the vessel wall by detecting the vessel wall by introducing an indicator through the introducer. This is a tube that extends 3 cm distal of the introducer tip with a side hole positioned 1 mm distal from the introducer tip. By pulling the introducer back and forth, the tip can be positioned at a desired position from the vessel wall by looking at blood dripping out from the indicator. This can be done without losing the entrance into the artery. Then, the anchor can be deployed near the puncture hole, 1 cm upstream, and the risk of getting the anchor caught upstream is reduced.

A technique used by Perclose (described in 5,613,974) is similar in that a channel through the device, with a side hole, is provided to visually detect blood emerging from the device handle to indicate the device position within the artery.

SUMMARY OF THE INVENTION

The invention addresses and solves two problems which occur in the sealing of punctures in blood vessels. The first problem is to detect the arterial wall in order to position the introducer tip at the correct location inside the vessel.

A second problem is to confirm that an inner seal itself is correctly positioned and is performing its sealing function.

In preferred embodiments of the invention, the position of a distal end of an introducer assembly in tissue is determined using a pressure sensor. The pressure sensor is connected to the proximal end of the introducer assembly. The introducer assembly has a fluid path between its distal end and its proximal end. Measured blood pressure is outputted as an indication of the position of the distal end of the introducer assembly in the tissue. Proper positioning of an inner seal is confirmed by placing the introducer assembly such that its distal end is in tissue outside a puncture in a blood vessel wall and observing a characteristic of blood at the proximal end of the introducer assembly. In this technique, a waveform of the blood pressure at the distal end of the introducer assembly may be displayed on a display to provide additional information to a surgeon as to the relative position of the components with respect to various tissues.

A pressure transducer is not needed to confirm that the puncture is sealed, since the flow of blood can be observed from an output port in the introducer if the puncture is not sealed. The output port can be, for example, a hole in the proximal end of the introducer, a clear tube connected to the proximal end of the introducer, or the like. However, providing a pressure transducer or pressure sensor, or a similar device, allows generation of pressure waveforms, or of a pulsation or pulsating signal that can be sensed, and thus provides additional information to the surgeon.

The occurrence of a pulsation or pulsating or oscillating signal or waveform guarantees that the distal end of the introducer has been safely inserted into an artery. If an introducer end by accident instead is introduced into a vein or is positioned in a puncture canal, the pressure transducer or sensor would indicate a non-pulsating signal or output, or at least a less pulsating signal or output, which readily can be distinguished from a signal/output arising from the markedly pulsating pressure prevailing in an artery.

DETAILED DESCRIPTION OF PREFERRED EMBODIMENTS

The invention provides an improved technique to detect the position of an introducer assembly in a blood vessel or tissue. According to this technique, an embodiment of the invention electronically (or optically) quantitatively measures the presence, amount (for example, absolute pressure), and/or waveform of blood pressure in the introducer, as opposed to merely visually detecting the presence of blood, as in the prior art. To accomplish this, a standard bedside blood pressure transducer is connected to the introducer's sidearm and the pressure (in for example mmHg)is displayed on a lab monitor.

In other embodiments of the invention, blood pressure is digitally sensed by a thumb or fingers or visually observed. For example, the pulsation of blood can be observed as an oscillating blood column or be digitally sensed or displayed by a moving needle or pointer.

The invention also provides a technique to detect the proper sealing of a puncture in a blood vessel wall. In this technique, after deploying an inner seal, the blood pressure in the tissue immediately outside of the seal is measured. If the puncture is not sealed (if, for example, the inner seal is caught upstream), significant blood pressure will still be indicated, and the seal can then be manipulated and twisted until it is released in the artery and can then be positioned properly.

When the inner seal is properly seated, the blood pressure will disappear. If the sealing is incomplete, a pressure will still be present, but at a lower level, and this indicates the need for, for example, harder tightening of the sealing elements.

The measured pressure waveform is displayed on the monitor to give the surgeon information as to the positioning of the various components relative to one another and relative to the various tissues. In addition, the pressure waveform can be analyzed electronically to provide the surgeon with further information.

Thus, the invention provides information regarding whether the introducer tip is in the artery, in the vessel wall, or outside the vessel. After apparent closure of the puncture, the pressure information provided by the invention indicates if the inner seal is tight or leaks. A small leak from the artery can be distinguished from tissue oozing by observing and/or analyzing the pressure waveform (for example, a pulsed waveform shape suggests a small leak). An artery leak indicates the need for better tightening of the seal. Tissue oozing requires no further action.

In a puncture closure device that has a seal inside the artery and a seal outside the artery (such as the FEMOSEAL™ seal), the invention can serve additional purposes. After deployment of the inner seal in the artery, the device is withdrawn until a resistance is felt. At that point, the inner seal should be seated over the inside of the puncture and the outer seal can then be deployed without risk of being deployed inside the artery. If the inner seal is caught upstream in the artery, without the invention, the surgeon may misinterpret the resistance (when the device is pulled) as an indication that the inner seal is seated over the puncture hole. However, with the invention, the fact that the inner seal is caught upstream in the artery will be detected by reading the pressure on the monitor.

FIGS. 1 to 14 illustrate various embodiments of the invention. These figures illustrate use of the invention in conjunction with the FEMOSEAL™ seal. However, the invention can be used in connection with a wide variety of seals other than the FEMOSEAL™ seal.

Figure 1:
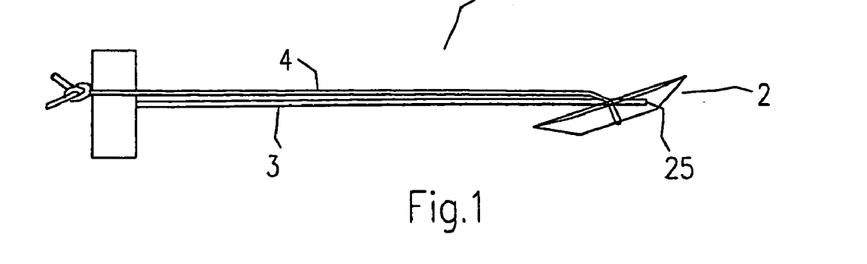
FIGS. 1 to 7 illustrate the design and operation of a first embodiment of the invention.
Figure 2:
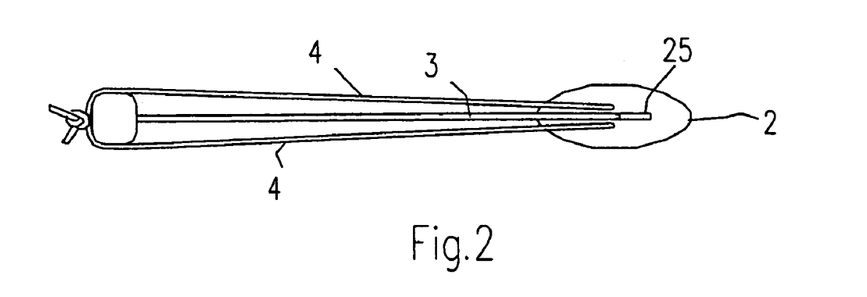
Figure 3:
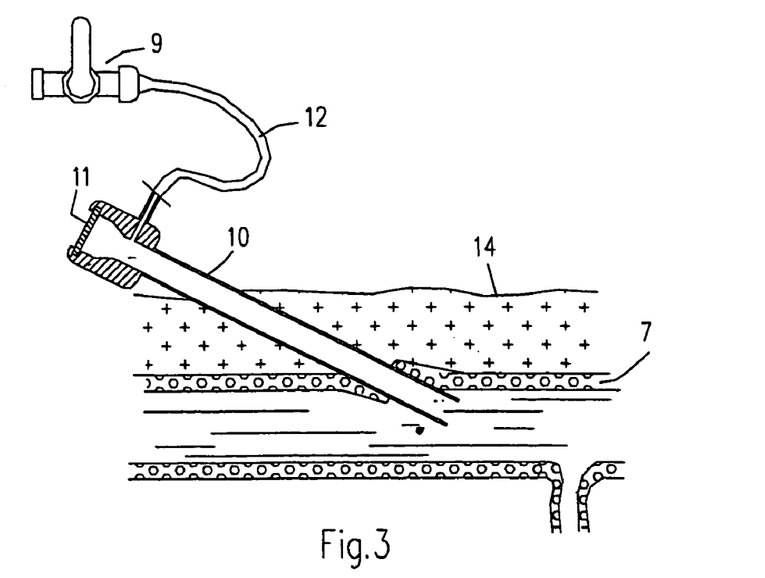

FIGS. 1 and 2 illustrate an apparatus 1 having an inner seal 2, a pusher 3 (with a tip 25), and a suture 4. FIG. 3 illustrates a sidearm 9 (with a stopcock in a closed position), an introducer 10, a hemostatic valve 11, and a tube 12, positioned with respect to artery wall 7 in tissue 14. Inner seal 2 performs two distinct functions. First, inner seal 2 seals the puncture in the blood vessel wall. Second, seal 2 holds an outer seal (not shown) in place. The above-identified patent application describes these components in further detail.

Figure 4:
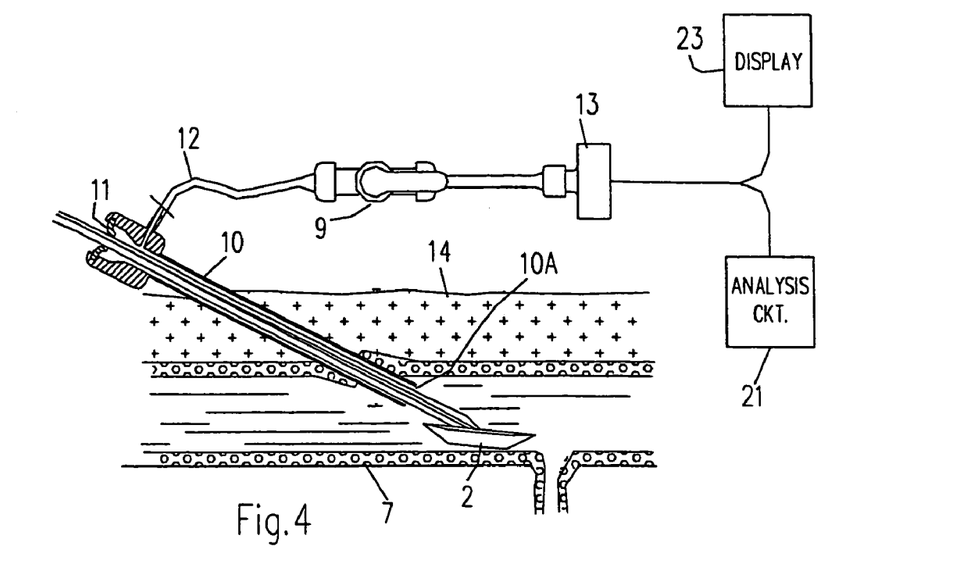

FIG. 4 shows inner seal 2 deployed within the artery, sidearm 9 (with a stopcock in an open position), and a pressure transducer 13. The pressure transducer 13 is in fluid communication with the distal tip 10A of introducer 10. Thus, in FIG. 4, transducer 13 senses normal arterial pressure. The pressure transducer can be any pressure transducer suitable for measuring blood pressure.

FIG. 4 also shows a display 23 to display pressure waveforms to the surgeon. The display can be any type of display or monitor. An analysis circuit 21 is also provided, which analyses the pressure data to output additional information to the surgeon.

Figure 5:
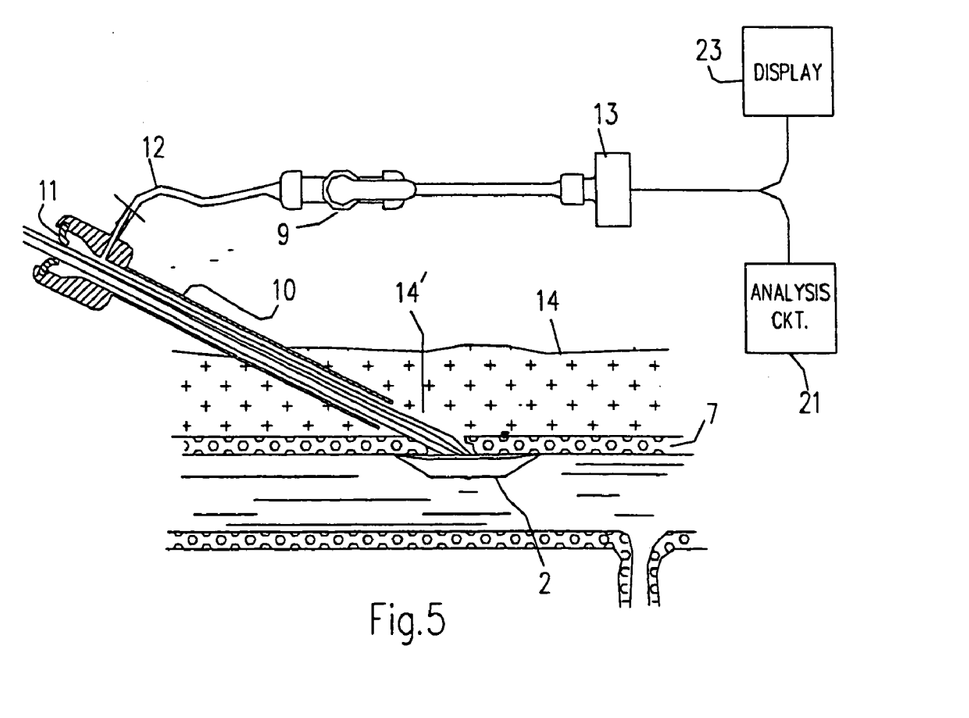

FIG. 5 shows the inner seal 2 properly seated to a puncture hole. In FIG. 5, transducer 13 senses essentially no normal arterial pressure and no normal pressure waveforms in the tissue 14' immediately outside of the seal. Thus, by monitoring the pressure (actually lack of pressure) via transducer 13, display 23, and/or analysis circuit 21, the surgeon can confirm that seal 2 is properly seated (that is, that seal 2 mates with the inner wall of the blood vessel in a leak tight fashion). If the sealing were incomplete, a pressure will still be present, but at a lower level, and this indicates the need for harder tightening of the sealing elements. The technique shown in FIG. 5 can also be employed to determine whether a seal which seals the puncture from outside the artery is properly positioned.

Figure 6:
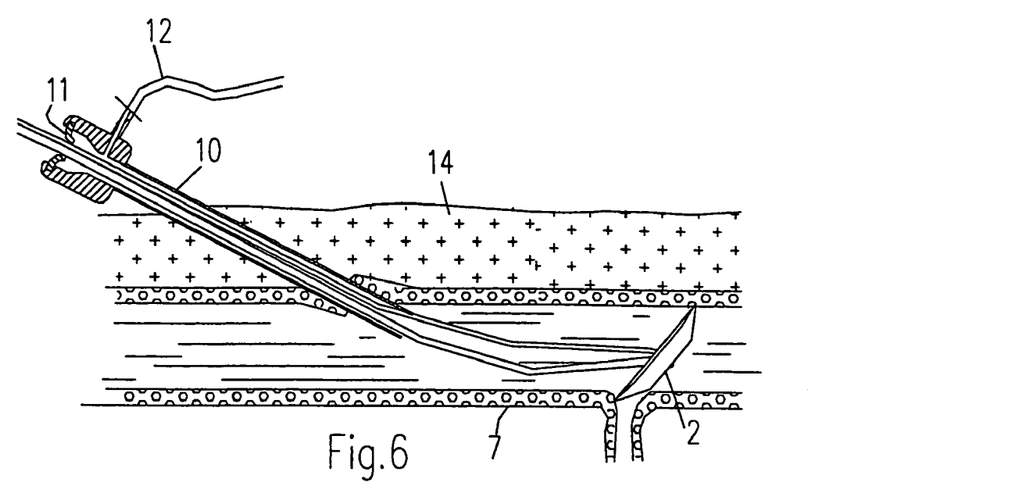

FIG. 6 shows seal 2 caught in an upstream branch. As described above, if the seal is caught upstream, blood pressure will still be indicated on the display (or monitor), and the seal can then be manipulated and twisted until it is released from the branch and can be seated to the puncture hole. In the FIG. 6 situation, when the surgeon pulls on sutures 4, the surgeon feels significant resistance and may wrongly believe (without use of the invention) that the seal is properly seated.

Figure 7:
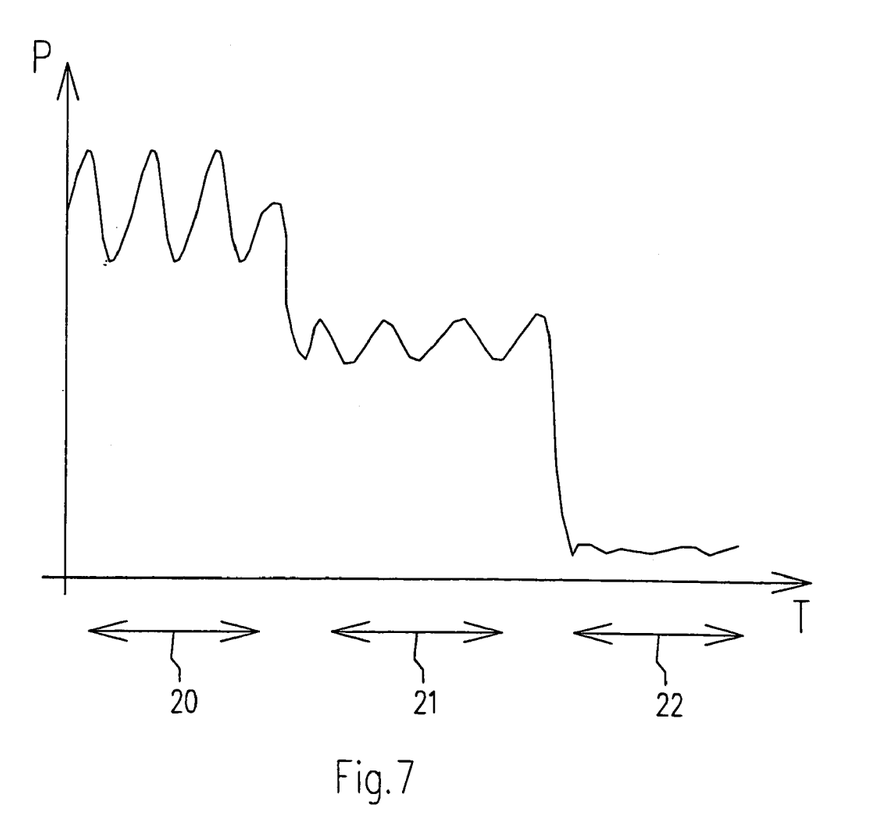

FIG. 7 illustrates examples of waveforms displayed on display 23. Waveform 20 corresponds to the situation when an inner seal is inside the blood vessel and an introducer is positioned as shown in FIG. 4. Waveform 22 corresponds to the situation when the inner seal is positioned as shown in FIG. 5. Waveform 21 corresponds to the situation when the sealing is incomplete.

Figure 8:
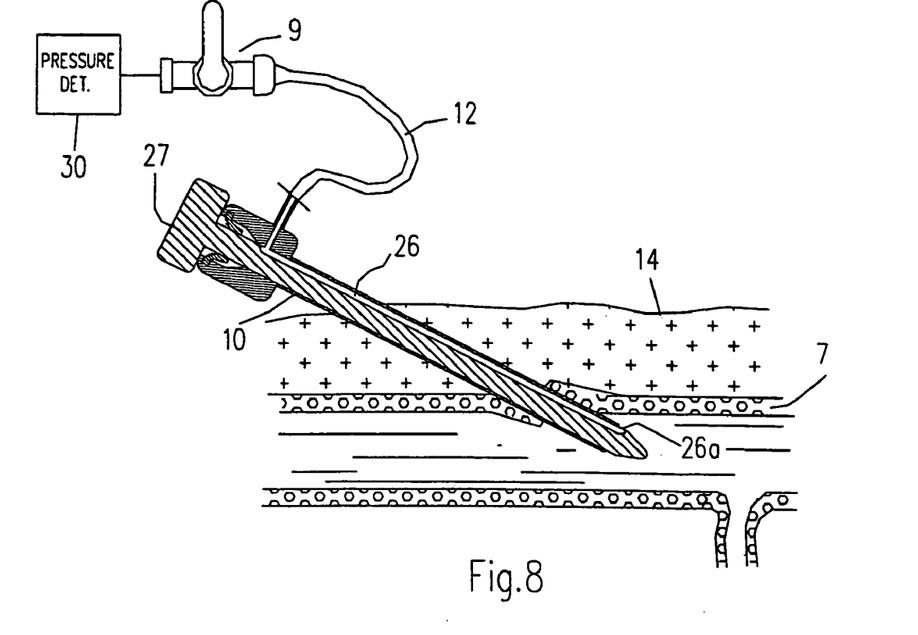
FIG. 8 illustrates a second embodiment of the invention.
Figure 9:
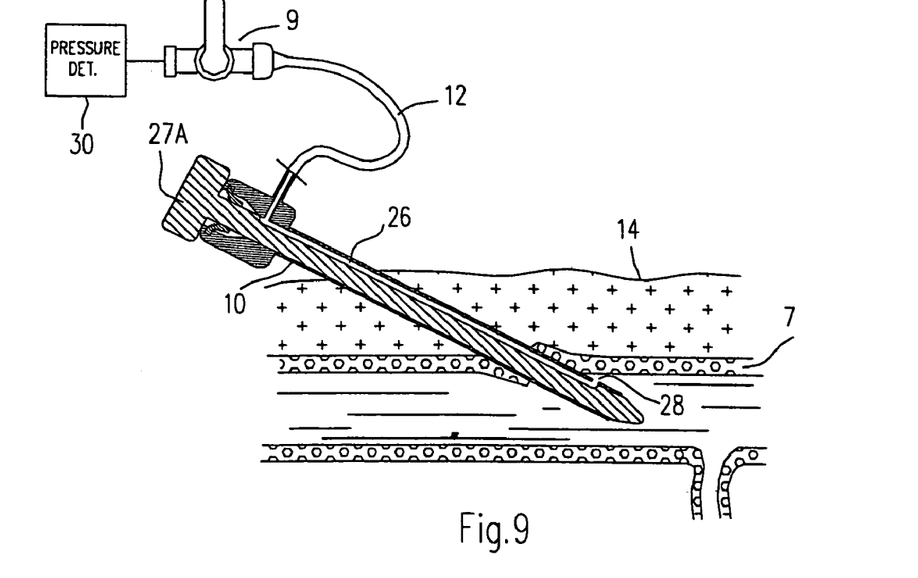
FIG. 9 illustrates a third embodiment of the invention.
Figure 10:
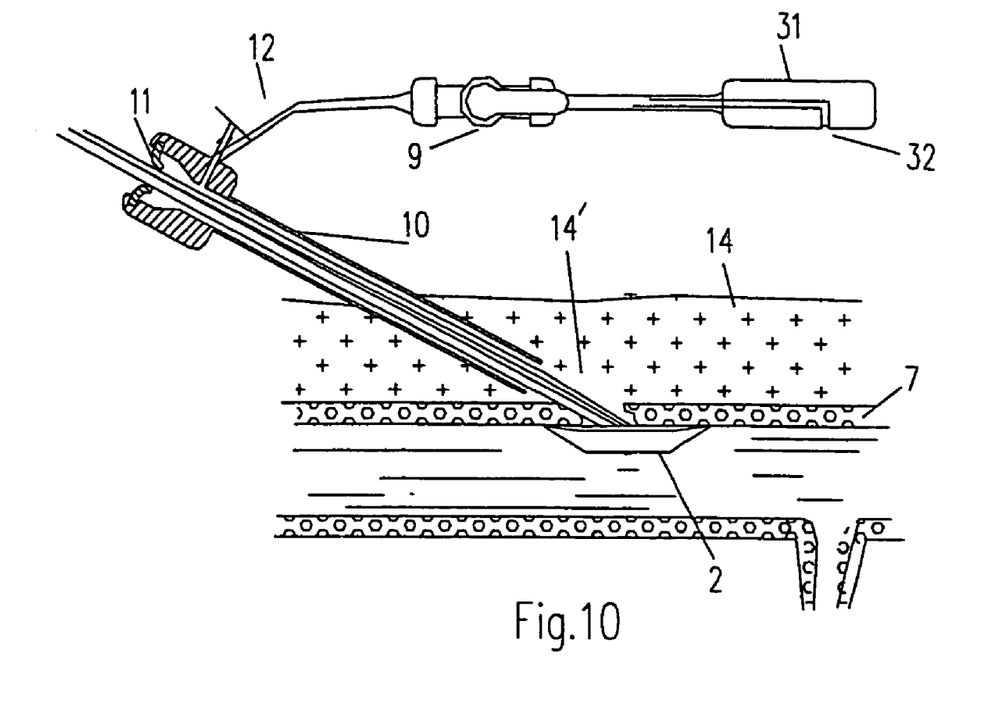
FIG. 10 illustrates a fourth embodiment of the invention.

FIGS. 8, 9, and 10 show second, third, and fourth embodiments of the invention.

FIG. 8 shows an introducer 10 with a core pin 27 inserted. The core pin (a dilator) has one channel 26 (or an axial grove) that communicates a tip opening 26a with the sidearm 9. With this technique, the introducer is pushed/pulled forward and backward until the opening 26a (or sidehole) is sealed by the vessel wall 7. This can be detected by a loss of pressure with pressure detector 30. The detector 30 is similar to transducer 13 and equipped with a display or audible indication of pressure, for example, an audible indication which varies as pressure varies. The detector is connectable, or adaptable, to the sidearm 9. Once it is confirmed that the introducer tip is positioned at the wall, the introducer can then be pushed forward into the vessel to a desired length. Then, the seal can be inserted into the introducer and deployed as close to the puncture site as possible.

FIG. 9 shows an introducer 33 with a core pin 27A inserted. The introducer has a sidehole 28 at a desired distance from the tip. With this design, the introducer can be positioned in a single operation by monitoring the pressure on detector 30, and the length that the introducer protrudes into the vessel is defined by the length from the sidehole to the introducer tip. For example, the introducer can be positioned by positioning hole 28 just inside the vessel wall by monitoring pressure on detector 30.

The technique shown in FIG. 10 is similar to the technique shown in FIG. 5, except that in FIG. 10, proper sealing of the inner seal 2 is determined by observing the absence of blood flow from an output port (or drip channel) 32 in an attachment 31.

Figure 11A:
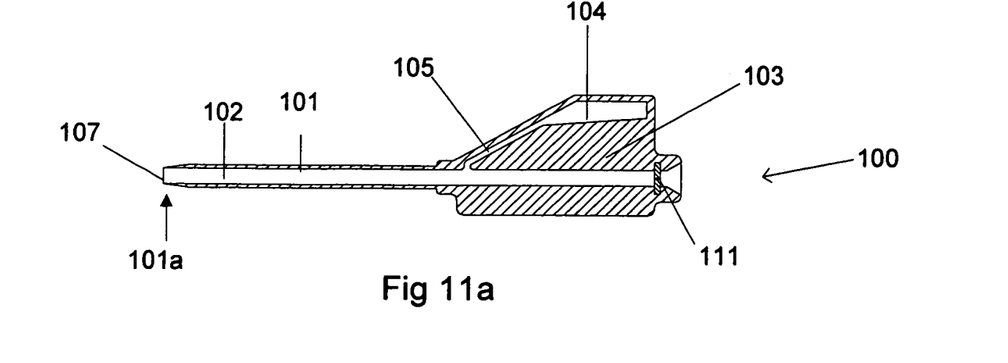
FIGS. 11a to 11e illustrate the design and operation of a fifth embodiment of the invention.

FIG. 11a discloses a further embodiment of a pressure monitoring system, in which a pressure transducer 100 comprises an introducer sheath 101 having a lumen 102. A housing 103 is provided at the proximal end of the introducer sheath 101. The housing 103 surrounds a proximal portion of the introducer sheath 101 and encloses a chamber 104, in which gas (air) is confined. The chamber 104 is in fluid communication with the lumen 102 of the introducer sheath 101 by a capillary or canal 105.

A hemostatic valve 111 is provided near the proximal end of lumen 102. At the very distal end 101a of lumen 102 an opening 107 is provided. The opening is (in this embodiment) circular in shape, has a diameter equal to the diameter of lumen 102, and lies in a plane perpendicular to the longitudinal axis of the lumen 102. The opening 107 allows use of a removable member (such as core pins 27 and 27A in FIGS. 8 and 9) which passes through the lumen 102. Such a removable member can, for example, provide for sensing of pressure at a specific location (based on the geometry of the removable member) as well as allows for unobstructed passage of other instruments through lumen 102.

Figure 11B:
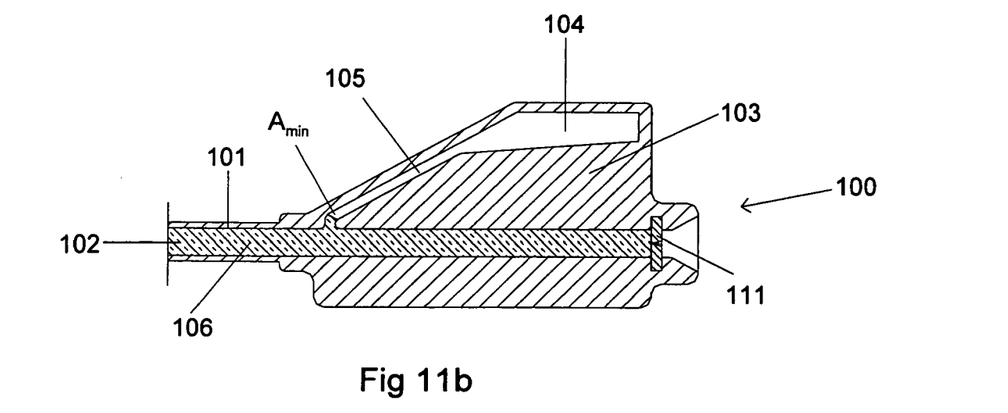
Figure 11C:
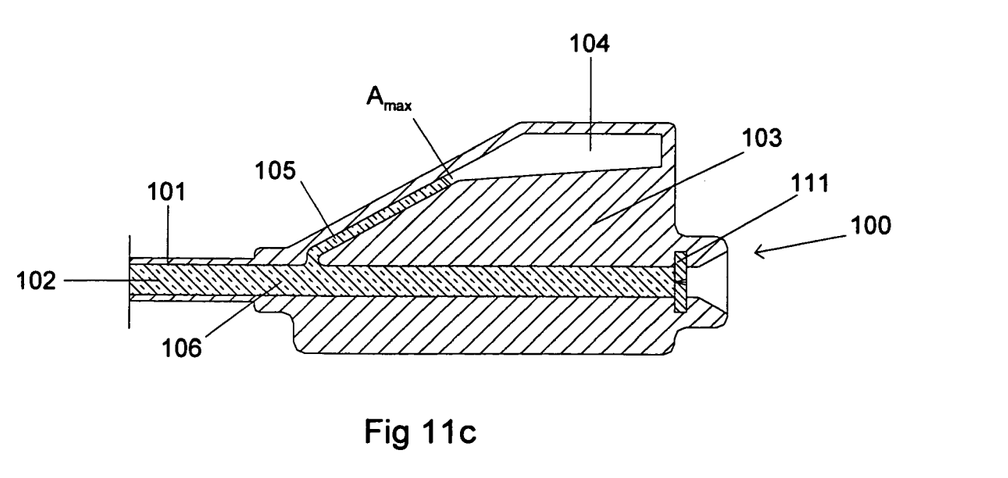
Figure 11D:
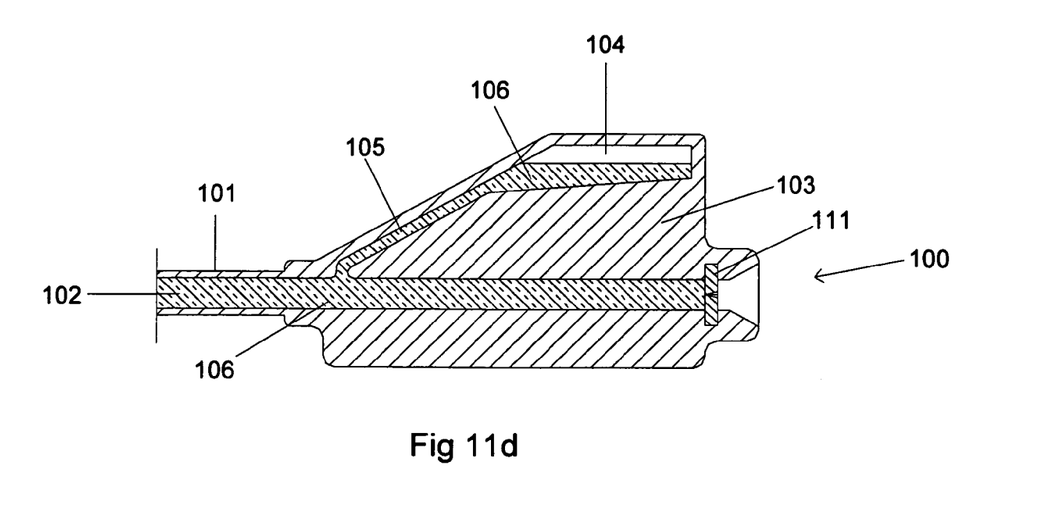

The proximal portion of the pressure transducer 100 according to FIG. 11a is shown in FIGS. 11b-d, and the function of the pressure transducer 100 will now be described with reference to these figures, starting with FIG. 11b. Blood 106 entering into the lumen 102 of the introducer sheath 101 will be diverted into the canal 105. Due to the counter-pressure created by the air trapped in the chamber 104, the blood meniscus will only reach into the canal 105 to an extent defined by this counter-pressure, i.e. until the blood pressure in an artery (or a vein or another body lumen) is in equilibrium with the air pressure in the chamber 104. When the distal end of the introducer sheath 101 is inside an artery, the blood meniscus in the canal 105 will oscillate or pulsate (herein the terms oscillate and pulsate have the same meaning) between two extremes, which in FIG. 11b and FIG. 11c have been indicated by $A_{min}$ and $A_{max}$, respectively. These two extremes $A_{min}$ and $A_{max}$ correspond preferably to the diastolic and systolic blood pressures, respectively. A normal value for the diastolic pressure may be within 70-80 mmHg, whereas the systolic pressure may be as high as 140 mmHg.

As is well known in the art, individual variations regarding blood pressure are large; and these variations are further affected in situations where the individuals are subjected to medical procedures including treatment with different drugs. But as a general rule, the total volume of the introducer lumen 102, the canal 105, and the chamber 104 is dimensioned such that the expected minimal diastolic pressure corresponds to a blood meniscus at $A_{min}$, and the expected maximal systolic pressure corresponds to a blood meniscus at $A_{max}$. In most applications, the exact positioning of $A_{min}$ and $A_{max}$ is, however, not very crucial, the important thing being that an oscillating blood meniscus can be observed. To provide for visually observing a blood meniscus oscillating in the canal 105, at least the portion of the housing 103 that covers the canal 105 should be made from a transparent material, such as plastic or glass or the like. Preferably, also the rest of the housing 103 can be made from a transparent material, to thereby make it possible to observe when and if blood enters into the lumen 102 of the introducer sheath 101 and/or into the chamber 104.

As mentioned above, blood pressure variations are large, and at severe hypertension the blood pressure can be higher than 180 mmHg. In FIG. 11d, a situation is illustrated wherein the blood pressure is so high that blood 106 enters into the chamber 104. Even in this situation, the counter-pressure caused by the air trapped inside the chamber 104 will, however, eventually create equilibrium and the blood meniscus will oscillate between two extremes. In other words, the pressure transducer 100 will also for extremely high blood pressures provide an oscillating blood column, which indicates that the distal end of the introducer sheath 101 is within an artery. Moreover, with suitable dimensions, the occurrence of blood within the chamber 104 will in itself guarantee that the distal end of the introducer sheath 101 is within an artery, because the blood pressure within an artery is the highest blood pressure in a human body and consequently all other blood pressures will be considerably lower, in practice so low that blood from other vessels or lumens will not be able to extend all the way into the chamber 104.

Figure 11E:
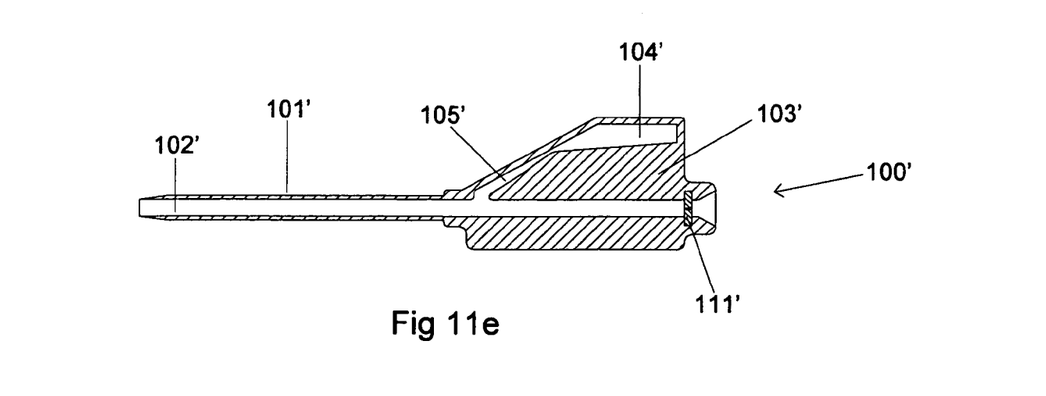

From the discussion in conjunction with FIGS. 11a-d, it may be realized that when the canal 105 has a uniform shape, the canal 105 will not linearly display the actual blood pressure. This means that for a given change in blood pressure, the blood meniscus will move a longer distance at the beginning or proximal portion of the canal 105 than at the more distal portions of the canal 105. FIG. 11e shows a pressure transducer 100', which schematically illustrates a way to eliminate this non-linearity. The pressure transducer 100' of FIG. 11e is identical with the pressure transducer 100 shown in FIGS. 11a-d except that a canal 105', which connects a lumen 102' of an introducer sheath 101' to a chamber 104', has been given a shape which tapers towards the chamber 104'. By selecting a suitable tapering for the canal 105', a given change in blood pressure—which always corresponds to a given change in the volume of the air trapped in front of the blood meniscus in the canal 105'—can be made to correspond to the same positional change of the blood meniscus throughout the canal 105'. A linear display of the blood pressure has thereby been accomplished.

In the situations illustrated in FIGS. 11b-d, blood 106 entering into the introducer sheath 101 completely fills the lumen 102 of the introducer 101, and fills in particular the portion of the introducer lumen 102 which is proximal of the entrance to the canal 105. If, however, air trapped in the proximal portion of the introducer sheath 101 would create a counter-pressure that is high enough to prevent the blood from reaching into the canal 105, no oscillating blood meniscus would, of course, be seen in the canal 105. To ensure that blood can reach to the beginning of the canal independently of the actual blood pressure, a small gas (air) leak can be provided at, for example, the proximal end of the introducer sheath 101. This leak should be so small that air can leak out from the introducer whereas blood is maintained within the introducer. However, as has been illustrated above in conjunction with FIGS. 3-6, a pressure transducer and an introducer are members of a larger assembly, and in practise, i.e. under all circumstances and after an extended period of storage, it can be difficult to ensure that such a small leak always is present.

Figure 12:
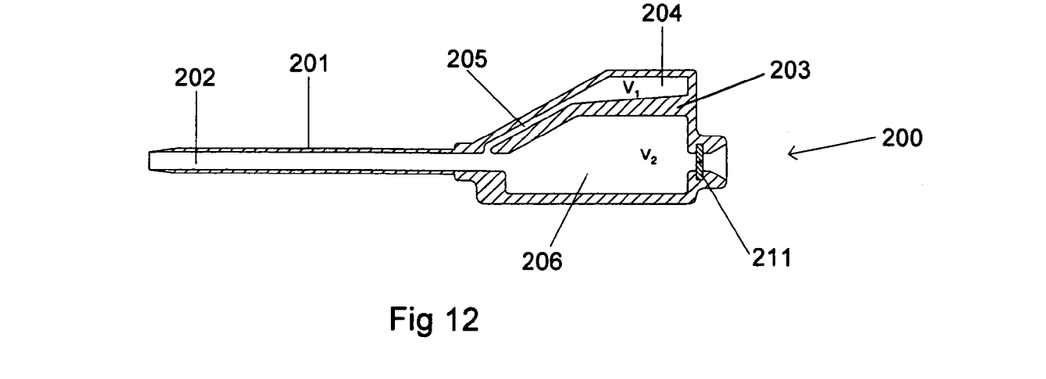
FIG. 12 illustrates a sixth embodiment of the invention.

FIG. 12 discloses a further embodiment of a pressure transducer 200 according to the present invention. The pressure transducer 200 comprises an introducer sheath 201 having a lumen 202. A housing 203 is provided at the proximal end of the introducer 201. The housing 203 surrounds a proximal portion of the introducer sheath 201, and encloses a first chamber 204, in which gas (air) is confined. The first chamber 204 is in fluid communication with the lumen 202 of the introducer 201 by a capillary or canal 205. The housing 203 further encloses a second chamber 206, in which the proximal end of the introducer lumen 202 ends. The volume of the first chamber has in FIG. 12 been designated by $V_1$, and the volume of the second chamber is designated by $V_2$. By having a large $V_2$, the counter-pressure created by the second chamber 206 against blood entering into the distal end of the introducer 201 is low, and it is hereby possible to design the pressure transducer 200 such that blood always can reach the opening into the canal 205. In fact, an air leak out from the second chamber 206 can be regarded as the special case where $V_2$ is infinitely large (from the air's point of view).

Figure 13:
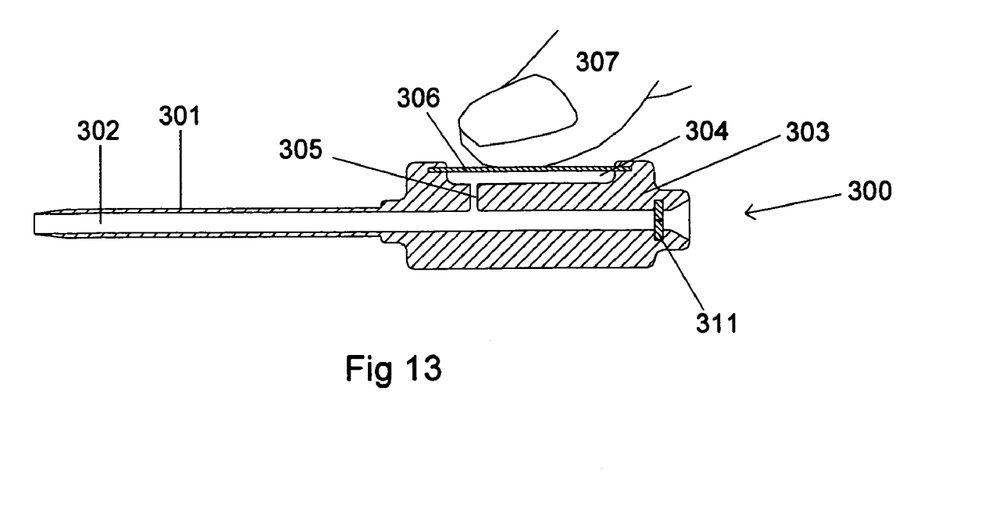
FIG. 13 illustrates a seventh embodiment of the invention.

Another embodiment of a pressure transducer 300 according to the present invention is shown in FIG. 13. Like the embodiments described above, the pressure transducer 300 comprises an introducer sheath 301 having a lumen 302, and a housing 303. The housing 303, which is provided at the proximal portion of the introducer sheath 301, encloses a chamber 304, which is in fluid communication with the introducer lumen 302 by a canal 305. A resilient membrane 306 constitutes an outer wall of the chamber 304. In use, the distal end of the introducer sheath 301 is introduced into an artery, which causes blood to flow into the chamber 304. The blood inside the chamber 304 will then pulsate between the diastolic and systolic pressures prevailing inside the artery. This pulsation will be transferred to the resilient membrane 306; and by placing a finger 307 on the resilient membrane 306, an operator can sense the pulsation and thereby determine that the distal end of the introducer sheath 301 actually is inside an artery (and not in a vein or other bodily lumen or tissue).

Figure 14:
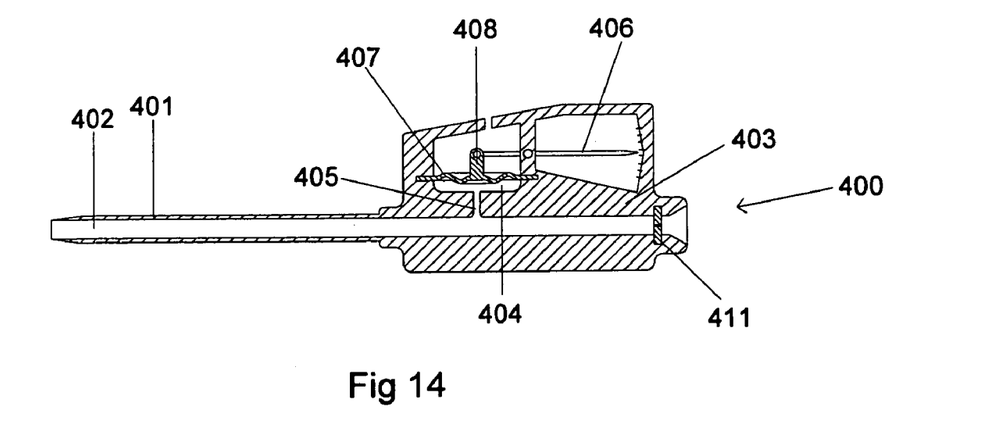
FIG. 14 illustrates an eighth embodiment of the invention.

Another type of pressure transducer is disclosed in FIG. 14. Here a pressure transducer 400 comprises an introducer sheath 401 having a lumen 402, a housing 403, which encloses a chamber 404, which is in fluid communication with the lumen 402 by a canal 405, and a pointer 406. A resilient membrane 407 is arranged inside the chamber 404, and is by a linkage 408 connected to the pointer 406. Blood having entered into the chamber 404 will hereby pulsate against the resilient membrane 407, and the linkage 408 will then transfer the pulsation to the pointer 406, to thereby provide an operator with a visual indication of the pulsating blood pressure.

The different embodiments of pressure transducers illustrated in conjunction with FIG. 11 to FIG. 14 represent closed systems, which means that there is no spillage of blood out from the pressure transducer. This is an advantage over devices that utilize a blood flow out from the device in order to indicate that an introducer is located inside an artery.

Further, like the pressure sensor illustrated in conjunction with FIGS. 4-9, the pressure transducers according to FIGS. 11-14 can be used for locating an artery as well as for verifying that an inner seal is correctly positioned against an artery wall, and for details regarding these different aspects of the invention, the reader is referred to the discussion above.

The invention is, of course, not limited to these specific embodiments. Modifications and variations of the invention will occur to those skilled in the field, after receiving the above teachings. The invention is therefore defined by reference to the following claims.

What is claimed is:

1. A system to sense the location of a distal portion of a member within a body, the system comprising:
   an introducer portion including:
      a lumen adapted to introduce an instrument therethrough, and
      a distal end adapted to be placed within a body, the distal end having an opening lying in a plane perpendicular to a longitudinal axis of the lumen and a proximal end having an opening lying in a plane perpendicular to the longitudinal axis of the lumen;
   a pressure sensor, in fluid communication via the lumen with the opening at the distal end, adapted to provide a pulsation which can be sensed by an operator when the distal end is placed within a pulsating portion of the body; and
   a core pin with a channel to provide said fluid communication, the core pin sized such that the core pin obstructs the opening at the distal end of the introducer so that the channel is the only flow path from the distal end of the introducer.

2. A system as set forth in claim 1, wherein the pulsation is visually displayed on a display.

3. A system as set forth in claim 1, further comprising a chamber to visually display pulsation.

4. A system as set forth in claim 3, wherein the chamber is a capillary tube.

5. A system as set forth in claim 1, wherein the distal end of the introducer portion is adapted to be positionable within a blood vessel.

6. A system as set forth in claim 1, further comprising a chamber which is not vented to atmosphere to visually display pulsation.

7. A system as set forth in claim 1, wherein the system comprises at least two chambers.

8. A system as set forth in claim 1, further comprising a member which vibrates due to the pulsation such that the vibration of the member can be sensed by touch.

9. A system as set forth in claim 1, further comprising a member which vibrates due to the pulsation such that the vibration can be visually observed.

10. A system as set forth in claim 1, wherein the pressure sensor comprises a pressure transducer.

11. A system to sense the location of a distal portion of a member within a body, the system comprising:
- an introducer portion including:
  - a lumen adapted to introduce an instrument therethrough, and
  - a distal end adapted to be placed within a body, the distal end having an opening lying in a plane perpendicular to a longitudinal axis of the lumen and a proximal end having an opening lying in a plane perpendicular to the longitudinal axis of the lumen, and
  - a side hole near the opening at the distal end of the introducer portion; and
- a pressure sensor, in fluid communication via the side hole and the lumen with the distal end, adapted to provide a pulsation which can be sensed by an operator when the distal end is placed within a pulsating portion of the body.

12. A system as set forth in claim 1, wherein the core pin further comprises an opening at an entrance to the channel.

13. A system as set forth in claim 12, wherein the opening lies in a plane perpendicular to the longitudinal axis of the lumen.

14. A system as set forth in claim 12, wherein the opening lies in a plane parallel to the longitudinal axis of the lumen.

15. A system to sense the location of a distal portion of a member within a body, the system comprising:
- an introducer portion having a lumen and a distal end adapted to be placed within a body;
- a core pin inserted in the introducer portion such that a distal end of the core pin passes beyond the distal end of the introducer portion, the core pin having a portion of reduced diameter such that a channel is formed between an inner wall portion of the introducer portion and an outer portion of the core pin, the channel having an entrance distal from the distal end of the introducer portion; and
- a pressure sensor, in fluid communication with the entrance via the channel, adapted to provide a pulsation which can be sensed by an operator when the entrance is placed within a pulsating portion of the body.

16. A system to sense the location of a distal portion of a member within a body, the system comprising:
- an introducer portion having a lumen and a distal end adapted to be placed within a body;
- a core pin inserted in the introducer portion such that a distal end of the core pin passes beyond the distal end of the introducer portion, the core pin having a portion of reduced diameter such that a channel is formed between an inner wall portion of the introducer portion and an outer portion of the core pin, the channel having an entrance proximal from the distal end of the introducer portion via an opening in the introducer portion; and
- a pressure sensor, in fluid communication with the entrance via the channel, adapted to provide a pulsation which can be sensed by an operator when the entrance is placed within a pulsating portion of the body.

17. A system to sense the location of a distal portion of a member within a body, the system comprising:
- an introducer portion having a lumen and a distal end adapted to be placed within a body;
- a core pin inserted in the introducer portion such that a distal end of the core pin passes beyond the distal end of the introducer portion, the core pin having a channel, the channel having an entrance distal from the distal end of the introducer portion, the core pin sized such that the core pin obstructs the distal end of the introducer portion so that the channel is the only flow path from the distal end of the introducer portion; and
- a pressure sensor, in fluid communication with the entrance via the channel, adapted to provide a pulsation which can be sensed by an operator when the entrance is placed within a pulsating portion of the body.

* * * * *

UNITED STATES PATENT AND TRADEMARK OFFICE
CERTIFICATE OF CORRECTION

PATENT NO. : 7,285,097 B2 Page 1 of 1
APPLICATION NO. : 10/798784
DATED : October 29, 2007
INVENTOR(S) : Tenerz et al.

It is certified that error appears in the above-identified patent and that said Letters Patent is hereby corrected as shown below:

Title page, item (*) notice: Delete "75 days" and insert --157 days--.

Signed and Sealed this

Third Day of February, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,285,097 B2 | Page 1 of 1 |
| APPLICATION NO. | : 10/798784 | |
| DATED | : October 23, 2007 | |
| INVENTOR(S) | : Tenerz et al. | |

It is certified that error appears in the above-identified patent and that said Letters Patent is hereby corrected as shown below:

Title page, item (*) notice: Delete "75 days" and insert --157 days--.

This certificate supersedes the Certificate of Correction issued February 3, 2009.

Signed and Sealed this

Twenty-fourth Day of February, 2009

JOHN DOLL
*Acting Director of the United States Patent and Trademark Office*